US007704468B1

(12) United States Patent
Klaehn et al.

(10) Patent No.: US 7,704,468 B1
(45) Date of Patent: Apr. 27, 2010

(54) METHOD FOR FORMING AN EXTRACTION AGENT FOR THE SEPARATION OF ACTINIDES FROM LANTHANIDES

(75) Inventors: John R. Klaehn, Idaho Falls, ID (US); Mason K. Harrup, Idaho Falls, ID (US); Jack D. Law, Pocatello, ID (US); Dean R. Peterman, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 767 days.

(21) Appl. No.: 11/232,541

(22) Filed: Sep. 21, 2005

(51) Int. Cl.
*C01G 56/00* (2006.01)
(52) U.S. Cl. .................. 423/9; 423/7; 423/21; 423/10
(58) Field of Classification Search ................ 423/10, 423/21, 9; 568/56
See application file for complete search history.

(56) References Cited

U.S. PATENT DOCUMENTS

| | | | | |
|---|---|---|---|---|
| 3,018,301 | A * | 1/1962 | Schrader ................. | 558/157 |
| 3,463,619 | A | 8/1969 | Ritter et al. | |
| 3,464,619 | A * | 9/1969 | Nordstrom ............. | 229/117.16 |
| 4,308,214 | A | 12/1981 | Robertson et al. | |
| 4,318,893 | A * | 3/1982 | Bathellier et al. ........... | 423/10 |
| 4,369,147 | A | 1/1983 | Michalski et al. | |
| 4,412,053 | A | 10/1983 | Neilson et al. | |
| 4,470,933 | A | 9/1984 | Michalski et al. | |
| 4,523,009 | A | 6/1985 | Neilson et al. | |
| 4,536,596 | A | 8/1985 | Savides et al. | |
| 4,548,790 | A * | 10/1985 | Horwitz et al. ............. | 423/9 |
| 4,721,605 | A | 1/1988 | Brown et al. | |
| 4,867,951 | A | 9/1989 | Smith et al. | |
| 5,447,552 | A | 9/1995 | Mihaylov et al. | |
| 5,475,146 | A | 12/1995 | Ayers et al. | |
| 5,639,433 | A * | 6/1997 | Yuan et al. ................ | 423/21.5 |
| 5,826,161 | A | 10/1998 | Madic et al. | |
| 5,908,805 | A * | 6/1999 | Huser et al. ................. | 502/53 |
| 5,966,584 | A * | 10/1999 | Modolo et al. ............... | 423/7 |
| 6,312,654 | B1 * | 11/2001 | Modolo et al. ............... | 423/10 |
| 2004/0124141 | A1 * | 7/2004 | Baron et al. ................ | 210/634 |
| 2004/0230079 | A1 * | 11/2004 | Prakash et al. .............. | 568/56 |
| 2005/0203314 | A1 | 9/2005 | Busacca et al. | |

FOREIGN PATENT DOCUMENTS

WO 2007037995 4/2007
WO 2008088576 7/2008

OTHER PUBLICATIONS

The separation of trivalent actinides from lanthanides by dithiophosphinic acids from HNO3, acid medium. By Giuseppe Modolo. Journal of Alloys and Compounds 271-273(1998)248-251.*
The preparation and coordination chemistry of phosphorous-slfur donor ligands. By jonathan R. Dilworth et al. Coordination Chemistry Reviews 199 (2000) 89-158.*
The Chemistry of Diphopshine Disulfides III. Influence of structure on the Course of Phosphinothioic Halide-Grignard Reactions. By N.k. Patel et al. (Department of Chemistry, The University of Akron, Ohio, 1967).*
Thermodynamic Study on the Synergistic Mixture of bis(chlorophenyl)dithiophosphinic acid and Tris(2-ethylhexyl0phsphate for Separation of Actinides(III) from lanthanides (III). By Giuseppe Modolo et al (Solvent extraction and ion Exchange 23, 3590373. 2005).*
Written Opinion of the International Searching Authority, International Application No. PCT/US 06/35807, International filing date Sep. 13, 2006.
Modolo et al., Thermodynamic Study on the Synergistic Mixture of Bis(chlorophenyl)dithiophosphinic Acid and Tris(2-ethylhexyl)phosphate for Separation of Actinides(III) from Lanthanides(III), Solvent Extraction and Ion Exchange; May 2005, vol. 23, Issue 3, pp. 359-373.
Romanovskiy et al., The Universal Solvent Extraction (UNEX) Process Development of the UNEX Process Solvent for the Separation of Cesuim, Strontium, and theAactinides from Acidic Radioactive Waste, Solvent Extraction and Ion Exchange, Jan. 2001, vol. 19. Issue 1, pp. 1-21.
Peterman et al., U.S. Appl. No. 11/530,508, filed Sep. 11, 2006, Actinide Extraction Methods and Actinide Separation Compositions.
International Search Report for PCT/US06/35807 dated Aug. 3, 2007.
Ionova, Rabbe et al., Solvent Extraction and Ion Exchange, 19(3), (2001), pp. 391-414.
Modolo, G., Influence of the Purity and Irradiation Stability of Cyanex 301, etc., Journal of Radioanalytical and Nuclear Chemistry, vol. 228, (1998), pp. 83-88.
Cowley, A., Preparation and Properties of Bulky Secondary Phosphines, Inorg. Chem., (1983), 22, pp. 547-550.
Higgins, Vogel & Craig, Aromatic Phosphinic Acids and Derivatives, etc., Journal of the American Chemical Society, (1954), pp. 1864-1866.
Benner, S., Diphenylphosphinodithioic Acid, etc., Tetrahedron Letters, vol. 22, No. 20, (1981), pp. 1851-1854.
Bartlett & Meguerian, Reactions of Elemental Sulfur, etc., Journal of the American Chemical Society, vol. 78, (1956), pp. 3710-3715.
Casalnuovo et al., Ligand Electronic Effects in Asymmetric Catalysis, etc., Journal of the American Chemical Society, 116, (1994), pp. 9869-9882.
Casey, et al., Electron Withdrawing Substituents on Equatorial and Apical Phosphines, etc., Journal of the American Chem. Soc., 119, (1997), pp. 11817-11825.
Peters, G., Reactions of Secondary Phosphine Sulfides, Journal of the American Chemical Society, vol. 27, (1961), pp. 2198-2201.

(Continued)

Primary Examiner—Melvin C Mayes
Assistant Examiner—Colette Nguyen
(74) Attorney, Agent, or Firm—TraskBritt

(57) ABSTRACT

An extraction agent for the separation of trivalent actinides from lanthanides in an acidic media and a method for forming same are described, and wherein the methodology produces a stable regiospecific and/or stereospecific dithiophosphinic acid that can operate in an acidic media having a pH of less than about 7.

42 Claims, No Drawings

OTHER PUBLICATIONS

Stuebe, et al., The Preparation and Reactions of Diphenylphosphinous Chloride, Journal of American Chemical Society, vol. 77, (1954), pp. 3526-3529.

Screttas et al., The Utilization of Organolithium Compounds, etc., Journal of American Chemical Society, vol. 27, (1962), pp. 2573-2577.

Hopkins, Vogel, Aromatic Phosphinic Acids and Derivatives, Journal of American Chemical Society, vol. 78, (1956), pp. 4447-4450.

Xie, Neilson et al., Organometallics, vol. 4, (1985), pp. 339-344.

Nash, K., A Comparison of New Reagents and Processes for Hydrometallurgical Processing of Actinides, Journal and date of Publication unknown.

Hays, H., The Controlled Alkylation of Mono-n-alkylphosphines, Journal of the American Chemical Society, vol. 31, (1966), pp. 3817-3820.

Kosolapoff, G., Some Variations of the Grignard Synthesis of Phosphinic Acids, Journal of the American Chemical Society, vol. 72, (1950), pp. 5508-5509.

Meier et al., Nonsymmetric palladium Complexes etc., Organometallics, vol. 22, (2003), pp. 3905-3914.

Guoxin et al., Investigation of the Extraction Complexes of Light Lanthanides, etc., Inorg. Chemistry, vol. 42, (2003), pp. 735-741.

Authors Unknown, Mitigation of Long Lived Actinides and Fission Products, ITU Annual Report (1997), pp. 83-95.

Dilworth & Wheatley, The Preparation and Coordination Chemistry of Phosphorus-Sulfur Donor Ligands, Coordination Chemistry Review, vol. 1999, (2000), pp. 89-158.

Pinkerton & Cavell, Synthesis and Characterization of Bis(trifluoromethyl)thiophosphinic Acid and its Anhydride, Journal of the American Chemical Society, vol. 94:6, (1972), pp. 1870-1874.

Cowley & Kemp, Preparation and Properties of Bulky Secondary Phosphines, Inorg. Chemistry, vol. 22, (1983), pp. 547-550.

Patel & Harwood, The Chemistry of Diphosphine Disulfides, The Journal of American Chemical Society, vol. 32, (1967), pp. 2999-3003.

Modolo & Odoj, Synergistic Selective Extraction of Actinides (III) Over Lanthanides, etc., Solvent Extraction and Ion Exchange, vol. 17(1), (1999), pp. 33-53.

Ionova et al., Mechanism of Trivalent Actinide/Lanthanide Separation Using Synergistic Mixtures, etc., New Journal of Chemistry, vol. 25, (2001), pp. 491-501.

International Search Report for International Application WO 2008/088576 (PCT/US2007/073229), Mailed Aug. 7, 2008.

Modolo et al., "The Separation of Trivalent Actinides from Lanthanides by Dithiophosphinic Acids from HNO3 Acid Medium," Journal of Alloys and Compounds, vols. 271-273 (1998) pp. 248-251.

\* cited by examiner

US 7,704,468 B1

METHOD FOR FORMING AN EXTRACTION AGENT FOR THE SEPARATION OF ACTINIDES FROM LANTHANIDES

GOVERNMENT RIGHTS

This invention was made with government support under Contract No. DE-AC07-05ID14517 awarded by the the United States Department of Energy. The government has certain rights in this invention.

CROSS-REFERENCE TO RELATED APPLICATION

This application is related to U.S. patent application Ser. No. 11/530,508, filed Sep. 11, 2006, pending.

TECHNICAL FIELD

The present invention relates to an extraction agent and a method for forming an extraction agent for the separation of actinides from lanthanides that produces a stable regiospecific and/or stereospecific dithiophosphinic acid that can operate in an acidic media having a pH of less than about 7.

BACKGROUND OF THE INVENTION

Those involved in the nuclear industry have long understood that a major obstacle to the expanded use of nuclear energy is the resulting generation of large quantities of spent nuclear fuel once the nuclear fuel cycle has been completed. Recent advanced aqueous reprocessing methods for spent nuclear fuel affords various methods for reducing waste generation and eliminating the proliferation potential in the nuclear fuel cycle. Those skilled in the art recognize that the fission products $^{137}$Cs and $^{90}$Sr are the major short term (less than 300 years) sources of heat load in spent fuel reprocessing streams. However, the trivalent actinides, those being primarily Americium and Curium are responsible for long term, that is, greater than about 1,000 years heat load that would reside in a geological repository. It has long been known that the separation of trivalent actinides via extraction agents, and subsequent recycle of these trivalent actinides to a nuclear reactor for transmutation, provides a means to safely and economically reduce the volume, heat generation, and radiotoxicity of waste material requiring geologic deposit. The obvious benefits from this technology would be extending the capacity for the Yucca Mountain Repository thus delaying or obviating the need for a second nuclear repository.

Heretofore, the commercially available extractant employed to separate trivalent actinides from trivalent lanthanides has been the product having the trade name CYANEX® 301, which is produced by Cytec Industries, Inc. This extractant is an effective agent for the separation of trivalent actinides (Am(III), Cm(III), etc.) from lanthanides in an acidic media.

While this extraction agent has worked with some degree of success, there are shortcomings with this compound that have detracted from its usefulness. Chief among these shortcomings is that this compound requires the use of mildly acidic processing conditions. In practice, the use of this compound requires complex feeding adjustments that complicates the operation of this very complex extraction process, and tends to increase the amount of secondary waste material. In addition to the foregoing, it has long been known that CYANEX® 301 is easily decomposed in acidic solutions, which further limit its usefulness in production scale processes.

An extraction agent and method for forming an extraction agent for the separation of actinides from lanthanides that avoids the shortcomings in the prior art compounds and methodology used heretofore is the subject matter of the present application.

SUMMARY OF THE INVENTION

Therefore, one aspect of the present invention is to provide an extraction agent for the separation of trivalent actinides from lanthanides in an acidic media that includes a stable regiospecific and/or stereospecific dithiophosphinic acid that can operate in an acidic media having a pH of less than about 7.

Another aspect of the present invention relates to a method for forming an extraction agent for the separation of actinides from lanthanides that includes providing a source of a first reagent having the formula P—(X)$_3$; providing a source of a second reagent having the formula R1-(M)X, and reacting the second reagent, with the first reagent having the formula P—(X)$_3$, to produce (X)$_2$—R1-phosphine; reacting (X)$_2$—R1-phosphine with a third reagent having the formula R2-(M)X to produce R2—R1—X-phosphine; reacting R2—R1—X-phosphine with a fourth metal hydride reagent having the formula (H)-M, wherein H comprises Hydrogen and M is a metal selected from the group comprising lithium, sodium, potassium, magnesium, calcium, boron, aluminum, and combinations thereof to produce R2—R1—H-phosphine; and providing a source of sulfur and reacting it with R2—R1—H-phosphine to produce R2—R1-dithiophosphinic acid.

Still another aspect of the present invention relates to a method for forming an extraction agent for the separation of actinides from lanthanides that includes providing a first reagent having the formula P—(X)$_2$—R$_{prot}$; providing a source of a second reagent having the formula R1-(M)X, and reacting it with the first reagent to produce R1—X—R$_{prot}$-phosphine; reacting the R1—X—R$_{prot}$-phosphine with a third reagent having the formula R2-(M)X to produce R2—R1—R$_{prot}$-phosphine; reacting the R2—R1—R$_{prot}$-phosphine with a fourth reagent having the formula H—X, wherein H comprises Hydrogen and X is a halogen to produce R2—R1—X-phosphine; reacting the R2—R1—X-phosphine with a fifth metal hydride reagent having the formula H-(M), wherein H comprises Hydrogen and M is a metal selected from the group comprising lithium, sodium, potassium, magnesium, calcium, boron, aluminum, and combinations thereof to produce R2—R1—H-phosphine; providing a source of a solvent comprising toluene; and providing a source of sulfur and reacting the source of sulfur with the R2—R1—H-phosphine and the toluene to produce R2—R1-dithiophosphinic acid.

Yet further, another aspect of the present invention relates to a method for forming an asymmetrical extraction agent for the separation of actinides from lanthanides in an acidic medium that includes providing a source of phosphorus trichloride; reacting a source of o-trifluoromethylphenylmagnesium bromide with the source of phosphorus trichloride to produce dichloro(o-trifluoromethylphenyl) phosphine; reacting the dichloro(o-trifluoromethylphenyl) phosphine with a source of n-octylmagnesium bromide to produce chloro(n-octyl)(o-trifluoromethylphenyl) phosphine; reacting the chloro(n-octyl)(o-trifluoromethylphenyl) phosphine with a source of lithium aluminum hydride to produce (n-octyl)(o-trifluoromethylphenyl) phosphine; and reacting a source of sulfur with the (n-octyl)(o-trifluoromethylphenyl) phosphine to produce (n-octyl)(o-trifluoromethylphenyl) dithiophosphinic acid.

Yet another aspect of the present invention relates to a method for forming an asymmetrical extraction agent for the separation of actinides from lanthanides in an acidic medium that includes providing a source of dichloro(diethylamino) phosphine reacting a source of o-trifluoromethylphenylmagnesium bromide with the source of dichloro(diethylamino) phosphine to produce chloro(diethylamino)(o-trifluoromethylphenyl) phosphine; reacting the chloro(diethylamino)(o-trifluoromethylphenyl) phosphine with a source of n-octylmagnesium bromide to produce (diethylamino)(n-octyl)(o-trifluoromethylphenyl) phosphine; reacting the (diethylamino)(n-octyl)(o-trifluoromethylphenyl) phosphine with a source of anhydrous hydrogen chloride to produce chloro(n-octyl)(o-trifluoromethylphenyl) phosphine; reacting the chloro(n-octyl)(o-trifluoromethylphenyl) phosphine with a source of lithium aluminum hydride to produce (n-octyl)(o-trifluoromethylphenyl) phosphine; and reacting a source of sulfur with the (n-octyl)(o-trifluoromethylphenyl) phosphine to produce (n-octyl)(o-trifluoromethylphenyl) dithiophosphinic acid.

A further aspect of the present invention relates to a method for forming an extraction agent for the separation of actinides from lanthanides that includes providing a first source of a reagent having the formula P—(X)$_2$—R$_{prot}$; providing a source of a second reagent having the formula R1-(M)X and reacting the second reagent with the first reagent to produce (R1)$_2$—R$_{prot}$-phosphine; reacting the (R1)$_2$—R$_{prot}$-phosphine with a third reagent having the formula H—X, wherein H comprises Hydrogen and X is a halogen, to produce (R1)$_2$—X-phosphine; reacting a fourth metal hydride reagent having the formula H-(M) with the (R1)$_2$—X-phosphine, wherein the H comprises Hydrogen and the M is a metal selected from the group comprising lithium, sodium, potassium, magnesium, calcium, boron, aluminum, and combinations thereof, to produce (R1)$_2$—H-phosphine; and providing a source of sulfur and reacting it with the (R1)$_2$—H-phosphine to produce (R1)$_2$-dithiophosphinic acid.

Still another aspect of the present invention relates to a method for forming an extraction agent for the separation of actinides from lanthanides that includes providing a first source of a reagent having the formula P—(X)$_3$; providing a source of a second reagent having the formula R1-(M)X and reacting the second reagent with the first reagent to produce (R1)$_2$—X-phosphine; reacting a third metal hydride reagent having the formula H-(M) with the (R1)$_2$—X-phosphine, wherein the H comprises Hydrogen, and M is a metal selected from group comprising lithium, sodium, potassium, magnesium, calcium, boron, aluminum, and combinations thereof, to produce (R1)$_2$—H-phosphine; and providing a source of sulfur and reacting it with the (R1)$_2$—H-phosphine to produce (R1)$_2$-dithiophosphinic acid.

Finally, another aspect of the present invention relates to a method of forming a symmetrical extraction agent for the separation of actinides from lanthanides in an acidic medium that includes providing a source of phosphorus trichloride; reacting a source of o-trifluoromethylphenylmagnesium bromide with the source of phosphorus trichloride to produce chloro(di-o-trifluoromethylphenyl) phosphine; reacting the chloro(di-o-trifluoromethylphenyl) phosphine with a source of lithium aluminum hydride to produce (di-o-trifluoromethylphenyl) phosphine; and reacting a source of sulfur with the (di-o-trifluoromethylphenyl) phosphine to produce (di-o-trifluoromethylphenyl) dithiophosphinic acid.

These and other aspects of the present invention will be described in greater detail hereinafter.

DETAILED DESCRIPTION OF THE INVENTION

This disclosure of the invention is submitted in furtherance of the constitutional purposes of the U.S. Patent Laws "to promote the progress of science and useful arts" (Article 1, Section 8).

To thoroughly understand the novelty of the present invention an understanding of the synthesis of a prior art extraction agent is helpful. As discussed above, the commercially available compound having the trade name CYANEX® 301 is currently employed in a highly complex extraction process to extract trivalent actinides from lanthanides. The synthesis of CYANEX® 301 is best understood by reference to the reaction noted below:

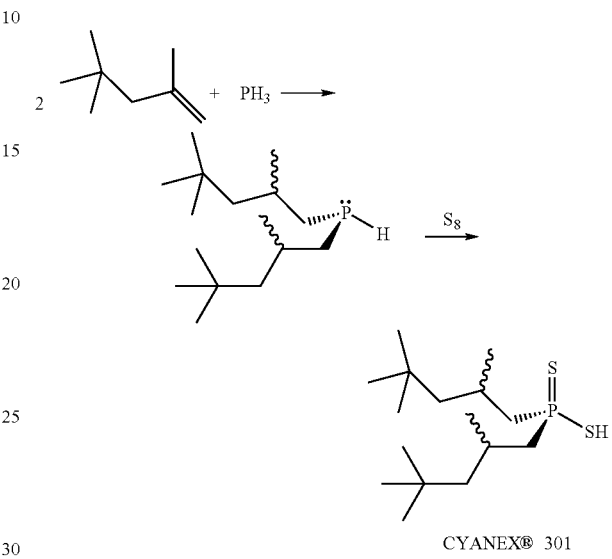

CYANEX® 301

It will be understood that CYANEX® 301 is synthesized in a two step process. Further, the present process has no stereoisomer control as represented by the wavy line that is positioned close to the phosphorus atom. In addition to the foregoing, the synthesis, noted above, is restricted to alkenes (that is, aliphatic groups). Still further, this compound is not very acidic for actinide metal extractions. As noted earlier, this same commercially available compound shows a degree of instability and decomposes readily in an acidic media. As currently commercially purchased, the product is only approximately 70% pure when purchased from the manufacturer Cytec Industries, Inc. Those skilled in the art have recognized that one of the major problems with CYANEX® 301 is that it is prone to degradation during the solvent extraction process.

Another prior art methodology for the separation of trivalent actinides from lanthanides is seen by reference to U.S. Pat. No. 6,312,654 to Modolo et al. (hereinafter referred to as the "Modolo Patent"), which issued on Nov. 6, 2001. The reaction as contemplated by the Modolo Patent is set forth below:

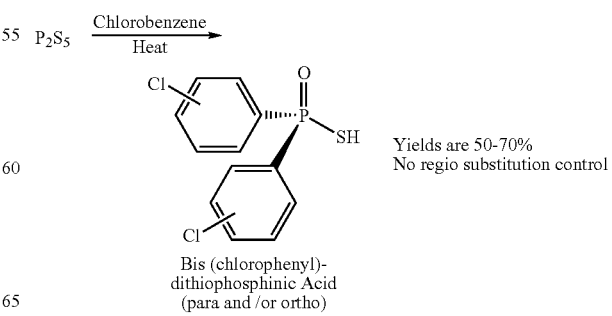

Bis (chlorophenyl)-dithiophosphinic Acid
(para and /or ortho)

The reaction, as noted above, has been typically referred to as a Higgins' Reaction, which was first described by W. A. Higgins in the Journal of American Chemical Society, 1955, 77, 1864. The Higgins' Reaction is best understood by the following:

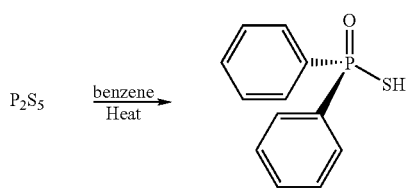

The Modolo Patent expands the Higgins' Reaction shown immediately above to produce a resulting compound as illustrated. Those skilled in the art have recognized that the reaction as contemplated by the Modolo Patent produces yields of only about 50-70%. Still further, the compound produced has no regiospecific substitution control. Other materials published by the author have indicated an approximate 50% overall yield using benzene only. In view of the fact that this reaction is not regiospecific selective, the resulting products will contain a mixture of both para and ortho compounds. Those skilled in the art have long recognized that the purification of ortho regiospecific products is often very difficult to obtain. The resulting product provided by the Modolo Patent does have certain advantages over the compound CYANEX® 301. As currently understood, the compound produced by the Modolo Patent appears to be water, acid, and radiation stable in contrast to CYANEX® 301. However, the compounds produced by the teaching of the Modolo Patent has certain disadvantages, including no extraction efficiency towards certain lanthanides and actinides by itself and further must use various synergists to get an extraction efficiency between certain actinides and lanthanides.

In the present invention, the inventors have discovered an extraction agent and methodology for forming an extraction agent for the separation of actinides in an acidic media that comprises a stable regiospecific and/or stereospecific dithiophosphinic acid, which can operate in an acidic media having a pH of less than about 7, and which avoids the shortcomings of the prior art discussed above. As presently conceived, the resulting dithiophosphinic acid may be symmetrical, or asymmetrical as will be discussed hereinafter. Yet further, the dithiophosphinic acid may be formed utilizing a single organometal reagent or two different organometal reagents. In this regard, the organometal reagent may have a formula R-(M)X, wherein M is a metal selected from the group comprising magnesium, lithium, sodium, aluminum, zinc, cadmium, mercury, copper, lead, thallium, and/or tin, wherein X is a halogen and R is an organic, which may have an inorganic component. The methodology of forming an extractant agent for the separation of actinides from lanthanides is shown in a first reaction, which is illustrated below:

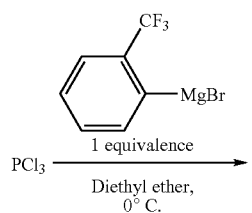

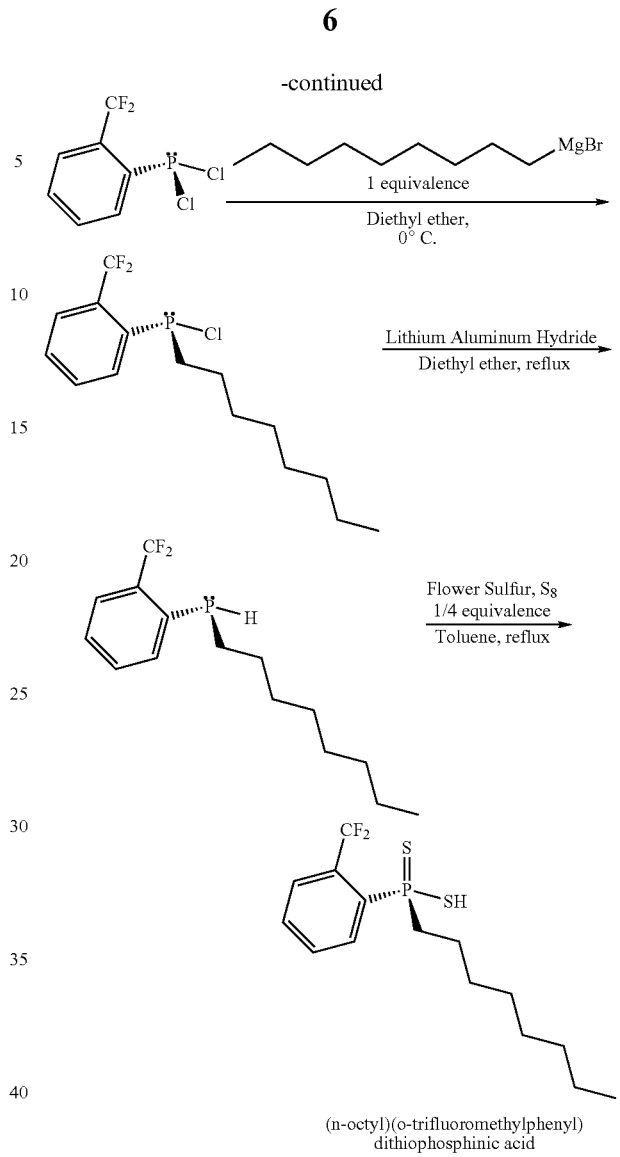

(n-octyl)(o-trifluoromethylphenyl) dithiophosphinic acid

The method as derived from the illustrated reaction, above, of forming an extraction agent for the separation of actinides from lanthanides comprises the steps of providing a source of a first reagent having the formula P—$(X)_3$; providing a source of a second reagent having the formula R1-(M)X, and reacting the second reagent with the first reagent having the formula P—$(X)_3$ to produce $(X)_2$—R1-phosphine; reacting $(X)_2$—R1-phosphine with a third reagent having the formula R2-(M)X to produce R2—R1—X-phosphine; reacting R2—R1—X-phosphine with a fourth metal hydride reagent having the formula (H)-M, wherein H comprises Hydrogen and M is a metal selected from the group comprising lithium, sodium, potassium, magnesium, calcium, boron, aluminum, and combinations thereof to produce R2—R1—H-phosphine; and providing a source of sulfur and reacting it with R2—R1—H-phosphine to produce R2—R1-dithiophosphinic acid.

As should be understood in the methodology as described above, $(X)_3$ is selected from the group comprising fluorine, chlorine, bromine, and iodine. In the methodology as described above, the method includes a further step of providing a source of a first solvent that comprises diethyl ether at a temperature of about 0° C. and reacting the first reagent having the formula P—(X)₃ and the second reagent having the formula R1-(M) X with the first solvent. Yet further, the methodology as described above includes another step of providing a source of a second solvent comprising diethyl ether at a temperature of about 0° C. and reacting the second solvent with the (X)₂—R1-phosphine and the R2-(M)X to produce the R2—R1—X-phosphine. In addition to the foregoing, the methodology further includes the step of providing a source of a solvent comprising diethyl ether at reflux and reacting the fourth metal hydride reagent, which comprises lithium aluminum hydride, and the R2—R1—X-phosphine to produce the R2—R1—H-phosphine. In the methodology as described above, R1 and R2 are selected from the group comprising alkyl, alkenyl, alkynyl and/or aryl compounds that have one to about 20 carbon atoms. As should be further understood, the alkyl, alkenyl, alkynyl and/or aryl compounds may include inorganic components that are selected from the group comprising oxygen, nitrogen, fluorine, chlorine, bromine, iodine, boron, gallium, silicon, germanium, phosphorus, arsenic, antimony, sulfur, selenium, tellurium, and oxides thereof. In the methodology as described above, the aryl compounds include both single and multiple ring compounds. In the methodology as described above, the R2—R1-dithiophosphinic acid is asymmetrical, and can operate in an acidic media having a pH of less than about 7.

More specifically, in the chemical reaction noted above, a methodology of forming an asymmetrical extraction agent for the separation of actinides from lanthanides in an acidic medium includes the steps of providing a source of phosphorus trichloride; reacting a source of o-trifluoromethylphenylmagnesium bromide with the source of phosphorus trichloride to produce dichloro(o-trifluoromethylphenyl) phosphine; reacting the dichloro(o-trifluoromethylphenyl) phosphine with a source of n-octylmagnesium bromide to produce chloro(n-octyl)(o-trifluoromethylphenyl) phosphine; reacting the chloro(n-octyl)(o-trifluoromethylphenyl) phosphine with a source of lithium aluminum hydride to produce (n-octyl)(o-trifluoromethylphenyl) phosphine; and reacting a source of sulfur with the (n-octyl)(o-trifluoromethylphenyl) phosphine to produce (n-octyl)(o-trifluoromethylphenyl) dithiophosphinic acid.

Another example of a method for forming an extraction agent for the separation of actinides from lanthanides is seen and understood by reference to the second chemical reaction identified below:

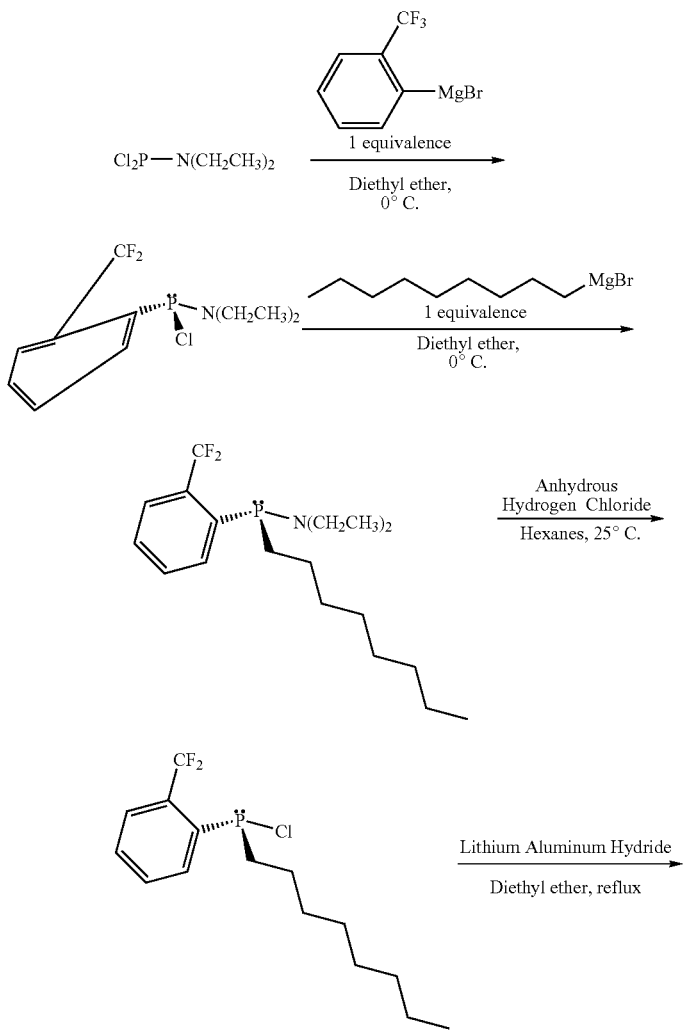

-continued

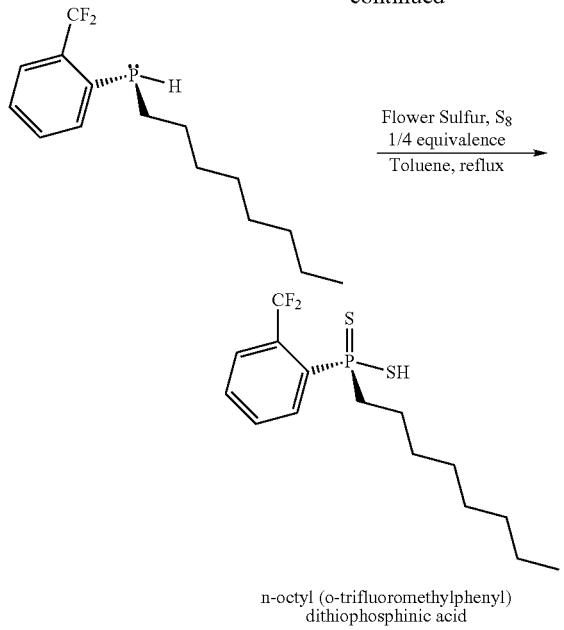

n-octyl (o-trifluoromethylphenyl)
dithiophosphinic acid

In the method for forming an extraction agent for the separation of actinides from lanthanides that is derived from the reaction shown above, the method includes the steps of providing a first reagent having the formula P—(X)$_2$—R$_{prot}$; providing a source of a second reagent having the formula R$_1$-(M)X and reacting it with the first reagent to produce R1—X—R$_{prot}$-phosphine; reacting the R1—X—R$_{prot}$-phosphine with a third reagent having the formula R2-(M)X to produce R2—R1—R$_{prot}$-phosphine; reacting the R2—R1—R$_{prot}$-phosphine with a fourth reagent having the formula H—X, wherein H comprises Hydrogen and X is a halogen to produce R2—R1—X-phosphine; reacting the R2—R1—X-phosphine with a fifth metal hydride reagent having the formula H-(M), wherein H comprises Hydrogen and M is a metal selected from the group comprising lithium, sodium, potassium, magnesium, calcium, boron, aluminum, and combinations thereof, to produce R2—R1—H-phosphine; providing a source of a solvent comprising toluene; and providing a source of sulfur and reacting the source of sulfur with the R2—R1—H-phosphine and the toluene to produce R2—R1-dithiophosphinic acid.

In the methodology as described in the paragraph immediately above, X is selected from the group comprising fluorine, chlorine, bromine, and iodine, wherein R$_{prot}$ is selected from the group comprising of organoamines having the formula R$_2$—N, wherein R comprises an alkyl having one to about five carbon atoms and N comprises Nitrogen. Further, the methodology as described above includes a step of providing a source of a first solvent comprising diethyl ether at a temperature of about 0° C. and reacting the first reagent having the formula P—(X)$_2$—R$_{prot}$ and the second reagent having the formula R1-(M)X with the diethyl ether. Yet further, the methodology as described above further includes the step of providing a source of a second solvent comprising diethyl ether at a temperature of about 0° C. and reacting it with the R1—X—R$_{prot}$-phosphine and the R2-(M)X to produce R2—R1—R$_{prot}$-phosphine.

In the methodology as described above, the method includes a further step of providing a source of a solvent comprising hexane at a temperature of about 25° C. and reacting the R2—R1—R$_{prot}$-phosphine and the fourth reagent having the formula H—X in the hexane to produce the R2—R1—X-phosphine. The methodology includes a further step of providing a source of diethyl ether at reflux and reacting the fifth metal hydride reagent, which comprises a source of lithium aluminum hydride, and the R2—R1—X-phosphine to produce the R2—R1—H-phosphine. Additionally, the methodology includes yet another step of providing a source of a solvent comprising toluene and reacting the source of toluene with the source of sulfur and the R2—R1—H-phosphine to produce the R2—R1-dithiophosphinic acid. In the methodology as described above, R1 and R2 are selected from the group comprising alkyl, alkenyl, alkynyl and/or aryl compounds that have one to about 20 carbon atoms. As with the first reaction described above for forming the stable regiospecific and/or stereospecific dithiophosphinic acid, the alkyl, alkenyl, alkynyl and/or aryl compounds may include inorganic components selected from the group comprising oxygen, nitrogen, fluorine, chlorine, bromine, iodine, boron, gallium, silicon, germanium, phosphorus, arsenic, antimony, sulfur, selenium, tellurium, and oxides thereof. As was the case with the first reaction, described earlier, the aryl compounds include both single and multiple ring compounds, and further, the R2—R1-dithiophosphinic acid is asymmetrical, and can operate in an acidic medium of less than about a pH of 7. In yet another alternative to the reaction noted above, it should be understood that R1 and R2 can be substantially the same reagent, wherein the resulting R2—R1-dithophosphinic acid is symmetrical and can operate in an acidic medium of less than about a pH of 7.

More specifically, the methodology as derived from the reaction discussed immediately above that is useful for forming an asymmetrical extraction agent for the separation of actinides from lanthanides in an acidic medium includes the steps of providing a source of dichloro(diethylamino) phosphine; reacting a source of o-trifluoromethylphenylmagnesium bromide with the source of dichloro(diethylamino) phosphine to produce chloro(diethylamino)(o-trifluoromethylphenyl) phosphine; reacting the chloro(diethylamino)(o-trifluoromethylphenyl) phosphine with a source of n-octyl-magnesium bromide to produce (diethylamino)(n-octyl)(o-trifluoromethylphenyl) phosphine; reacting the (diethylamino)(n-octyl)(o-trifluoromethylphenyl) phosphine with a source of anhydrous hydrogen chloride to produce chloro(n-octyl)(o-trifluoromethylphenyl) phosphine; reacting the chloro(n-octyl)(o-trifluoromethylphenyl) phosphine with a source of lithium aluminum hydride to produce (n-octyl)(o-trifluoromethylphenyl) phosphine; and reacting a source of sulfur with the (n-octyl)(o-trifluoromethylphenyl) phosphine to produce (n-octyl)(o-trifluoromethylphenyl) dithiophosphinic acid.

Another aspect of the methodology of forming an extraction agent for the separation of actinides from lanthanides is shown in the third reaction noted below:

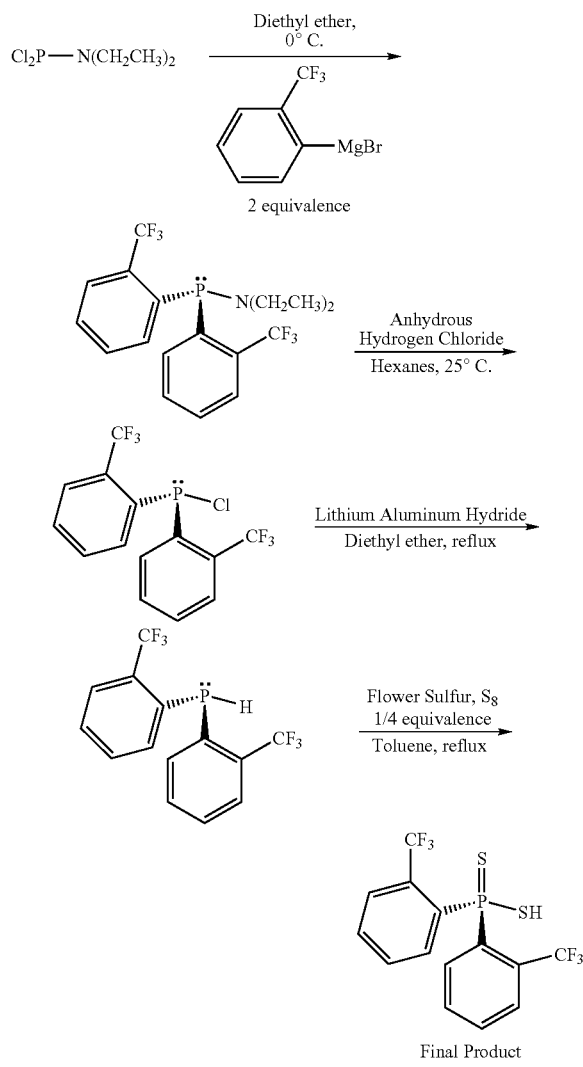

As seen in the third reaction, noted above, the method for forming an extraction agent for the separation of actinides from lanthanides includes the steps of providing a source of a first reagent having the formula P—(X)$_2$—R$_{prot}$; providing a source of a second reagent having the formula R1-(M)X and reacting the second reagent with the first reagent to produce (R1)$_2$—R$_{prot}$-phosphine; reacting the (R1)$_2$—R$_{prot}$-phosphine with a third reagent having the formula H—X, wherein H comprises Hydrogen and X is a halogen to produce (R1)$_2$—X-phosphine; reacting a fourth metal hydride reagent having the formula H-(M) with the (R1)$_2$—X-phosphine, wherein the H comprises Hydrogen and the M is a metal selected from the group comprising lithium, sodium, potassium, magnesium, calcium, boron, aluminum, and combinations thereof, to produce (R1)$_2$—H-phosphine; and providing a source of sulfur and reacting it with the (R1)$_2$—H-phosphine to produce (R1)$_2$-dithiophosphinic acid.

As seen in the third reaction, noted above, the resulting R1—R2-dithiophosphinic acid is symmetrical and can operate in an acidic media of less than about 7. Still further, in the reaction noted in the paragraph immediately above, X is selected from the group comprising fluorine, chlorine, bromine, and iodine, wherein the R$_{prot}$ is selected from the group comprising organoamines having the formula R$_2$—N, wherein R comprises an alkyl having one to about five carbon atoms and N comprises Nitrogen. Additionally, the method further includes the step of providing a source of a first solvent comprising diethyl ether at a temperature of about 0° C. and reacting it with the first and second reagents. The method also includes the step of providing a source of a second solvent comprising diethyl ether at a temperature of about 0° C. and reacting it with the fourth metal hydride reagent and the (R1)$_2$—X-phosphine to produce the (R1)$_2$—H-phosphine. The method also includes an additional step of providing a source of a solvent comprising hexane at a temperature of about 25° C. and reacting the (R1)$_2$—R$_{prot}$-phosphine and the third reagent to produce the (R1)$_2$—X-phosphine. In the methodology as described above, R1 is selected from the group comprising alkyl, alkenyl, alkynl, and/or aryl compounds that have one to about 20 carbon atoms. Additionally, it will be noted that the alkyl, alkenyl, alkynyl, and/or aryl compounds may include inorganic components selected from the group comprising oxygen, nitrogen, fluorine, chlorine, bromine, iodine, boron, gallium, silicon, germanium, phosphorus, arsenic, antimony, sulfur, selenium, tellurium, and oxides thereof. As was described above with respect to the other previously disclosed chemical reactions, the aryl compounds include both single and multiple ring compounds.

The method for forming an extraction agent for the separation of actinides from lanthanides as discussed above, may also include other steps including providing a first source of a reagent having the formula P—(X)$_3$; providing a source of a second reagent having the formula R1-(M)X and reacting the second reagent with the first reagent to produce (R1)$_2$—X-phosphine; reacting a third metal hydride reagent having the formula H-(M) with the (R1)$_2$—X-phosphine, wherein the H comprises Hydrogen and M is a metal selected from group comprising lithium, sodium, potassium, magnesium, calcium, boron, aluminum, and combinations thereof, to produce (R1)$_2$—H-phosphine; and providing a source of sulfur and reacting it with the (R1)$_2$—H-phosphine to produce (R1)$_2$-dithiophosphinic acid. In the methodology as described in this paragraph, the (R1)$_2$-dithiophosphinic acid is symmetrical and can operate in an acidic medium at a pH of less than about 7. As with the previously described reactions, X is selected from the group comprising fluorine, chlorine, bromine, and iodine. Further, the methodology as described above includes a step of providing a source of a first solvent comprising diethyl ether at a temperature of about 0° C. and reacting it with the first and second reagents to produce (R1)$_2$—X-phosphine. In addition to the foregoing, the methodology includes another step of providing a source of a second solvent comprising diethyl ether at a temperature of about 0° C. and reacting the second solvent with the fourth metal hydride reagent and the $(R1)_2$—X-phosphine to produce the $(R1)_2$—H-phosphine. Moreover, R1 is selected from the group comprising alkyl, alkenyl, alkynyl, and/or aryl compounds that have one to about 20 carbon atoms, wherein the alkyl, alkenyl, alkynyl, and/or aryl compound may include inorganic components selected from the group comprising oxygen, nitrogen fluorine, chlorine, bromine, iodine, boron, gallium, silicon, germanium, phosphorus, arsenic, antimony, sulfur, selenium, tellurium, and oxides thereof. As was the case with the other reactions noted above, the aryl compounds include both single and multiple ring compounds.

The present invention contemplates a methodology of forming a symmetrical extraction agent for the separation of actinides from lanthanides in an acidic medium, which includes the steps of providing a source of phosphorus trichloride; reacting a source of o-trifluoromethylphenylmagnesium bromide with the source of phosphorus trichloride to produce chloro(di-o-trifluoromethylphenyl) phosphine; reacting the chloro(di-o-trifluoromethylphenyl) phosphine with a source of lithium aluminum hydride to produce (di-o-trifluoromethylphenyl) phosphine; and reacting a source of sulfur with the (di-o-trifluoromethylphenyl) phosphine to produce (di-o-trifluoromethylphenyl) dithiophosphinic acid.

Examples of the synthesis of the stable regiospecific and/or stereo dithiophosphinic acid of the present invention are provided below:

Synthesis of Di-(3,5-Bis(trifluoromethyl)phenyl)dithiophosphinic Acid

The following examples are by reference to the chemical reaction identified as Schemes 1 and 2 below. With reference to Scheme 1, an approximate 1.0 M solution of a starting Grignard reagent was synthesized (1). Magnesium metal shavings ($Mg^0$, 4.9 g; 0.20 mol) were placed into a 250-mL round-bottom flask. The flask was equipped with a gas inlet adapter and magnetic stir bar. This system was placed under vacuum and the system was then purged with nitrogen. First, 171 mL of an anhydrous diethyl ether was transferred to the flask by syringe, and then 50 g (0.171 mol) of $3,5$-$(CF_3)_2C_6H_3Br$ (2) was introduced by syringe. The solution was stirred during the reaction. An ice bath was needed to cool down the reaction as the magnesium was consumed. After most of the magnesium metal was consumed, the reaction mixture was allowed to set overnight under nitrogen.

After the procedure discussed above, and by reference to Scheme 2, a 500-mL three-neck, round-bottom flask, equipped with a gas inlet; a 125-mL addition funnel; magnetic stir bar, and a rubber septum was charged with nitrogen, $Cl_2P$—$N(CH_2CH_3)_2$ (3) 10 g, 0.058 mol), and anhydrous diethyl ether (300 mL). The solution was cooled to 0° C., and a Grignard reagent [$3,5$-$(CF_3)_2C_6H_3MgBr$ (2)] (~1.0 M in diethyl ether, 117 mL, 0.117 mol) was added to the addition funnel via syringe. The compound (2) was added to the cooled solution. After finishing, the addition funnel was removed and replaced with a stopper. The ice bath was removed and the mixture was allowed to warm to room temperature while stirring overnight. The next day, approximately ~75% of the ether was removed under reduced pressure, leaving behind a slurry. The slurry was washed three times with 200 mL of hexanes to precipitate the salts. The supernatant, $(3,5$-$(CF_3)_2C_6H_3)_2Cl_2P$—$N(CH_2CH_3)_2$ (4), was decanted into a nitrogen-purged 1000-mL round-bottom flask equipped with a magnetic stir bar.

Using the previous setup, six equivalents of 2.0 M hydrogen chloride in diethyl ether (150 mL; 0.20 mol) was introduced to the isolated phosphine $(3,5$-$(CF_3)_2C_6H_3)_2Cl_2P$—$N(CH_2CH_3)_2$ (4) in hexanes via syringe. The solution stayed at room temperature, stirring, under nitrogen. The amine salt formed during a 2-4 hour time span. This salt was separated by airless filtration, and the solution was concentrated by the removal of excess hexanes under nitrogen. The concentrated solution was purified by vacuum distillation at 0.10 to 0.20 mmHg/83° C. to give $(3,5$-$(CF_3)_2C_6H_3)_2P$—Cl (5) as a colorless liquid. Isolated yields of compound (5) were roughly 72% with good purity.

Following the reaction noted above, a three-neck 250-mL round-bottom flask was equipped with a water-jacketed condenser, gas inlet adapter, tow stoppers, and magnetic stir bar. The system was then purged with nitrogen. Anhydrous diethyl ether (100 mL) was transferred to the flask, via syringe. $LiAlH_4$ (0.57 g, 0.015 mol) was introduced into the flask and cooled to −78° C.; $(3,5$-$(CF_3)_2C_6H_3)_2P$—Cl (5) (5.0 g, 0.0011 mol) was slowly added to the cooled flask by syringe. The gray slurry that resulted was refluxed for about 2 hours, cooled to 0° C., and slowly hydrolyzed with 10 wt % aqueous $NH_4Cl$. The organic layer was separated, and the remaining white precipitate was extracted three times with 25 mL of diethyl ether. The combined ether extracts were dried with $Na_2SO_4$, filtered and evaporated to give $(3,5$-$(CF_3)_2C_6H_3)_2P$—H (6) as a pale yellow air-sensitive solid. The purification was conducted by sublimation at 0.07 to 0.10 mmHg/100-130° C., which gave $(3,5$-$(CF_3)_2C_6H_3)_2P$—H (6) as a white solid. A small amount of the side-product (phosphine oxide) was carried across with the product. A $^{31}P$ NMR subsequently showed compound (6) as the dominate peak (90-95%). The yields were estimated at about 50%.

The final reaction was as follows: a 100-mL round-bottom flask was equipped with a water-jacketed condenser, gas inlet adaptor, and magnetic stir bar. The system was purged with nitrogen. A slight excess of sulfur flower ($S_8$; 0.15 g, 0.006 mol) was used with this reaction, and anhydrous toluene (50 mL) was transferred to the flask, via syringe. A solution of $(3,5$-$(CF_3)_2C_6H_3)_2P$—H (6) (1.0 g, 0.002 mol) in anhydrous toluene (25 mL) was slowly added to the flask by syringe. The reaction was refluxed vigorously to yield $(3,5$-$(CF_3)_2C_6H_3)_2PS_2H$ (7) in about 24 hours. The reaction was cooled to room temperature and the excess sulfur was filtered. Toluene was evaporated by reduced pressure to give a greenish-white solid. The solid residue was dissolved in petroleum (PET) ether and more sulfur precipitated out of solution. The PET ether solution was filtered again to give a green solution. The PET ether was removed by reduced pressure to give a greenish-white solid. The final product, $(3,5$-$(CF_3)_2C_6H_3)_2PS_2H$ (7), has a $^{31}P$ NMR at 50 ppm. The product could be purified by vacuum distillation. Compound (7) distilled at 0.08-0.06 mmHg/120-130° C. It should be noted that the product needed to be "flashed" (heated glass) across to stop the product from solidifying in the distillation apparatus. It distilled as a slight greenish-white, amorphous solid. It can be crystallized in hexanes to give clear, transparent, hexagonal crystals. The final product yields for this reaction were variable between 30-62%. The resulting Di-(3,5-Bis(trifluoromethyl)phenyl)dithiophosphinic Acid (7) had the following characteristics: 62% yield; mp=72-74° C.; bp=0.06-0.08 mmHg/120-130° C.; $^{31}P$ NMR δ ($CDCl_3$)=(s) 50.0; $^1H$ NMR δ ($CDCl_3$)=(d, $J_{PH}$=14.4 Hz, 2H) 8.43, (s, H) 8.11, (s, H) 2.84; $^{13}C$ NMR δ ($CDCl_3$)=(doublet, $J_{PC}$=86.0 Hz, ipso) 138.4, (doublet of quartets, $J_{PC}$=13.8 Hz, $J_{CF}$=34.2 Hz, meta) 133.3, (doublet, $J_{PC}$=10.8 Hz, ortho) 131.4, (doublet, $J_{PC}$=3.1 Hz, para) 127.0, and (quartet, $J_{CF}$=271.8 Hz, $CF_3$) 123.0.

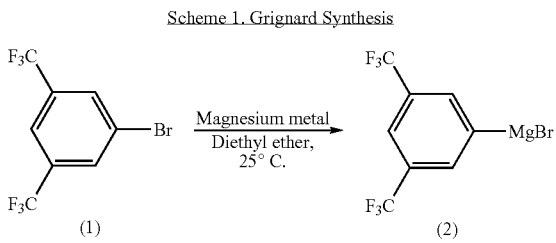

Scheme 1. Grignard Synthesis

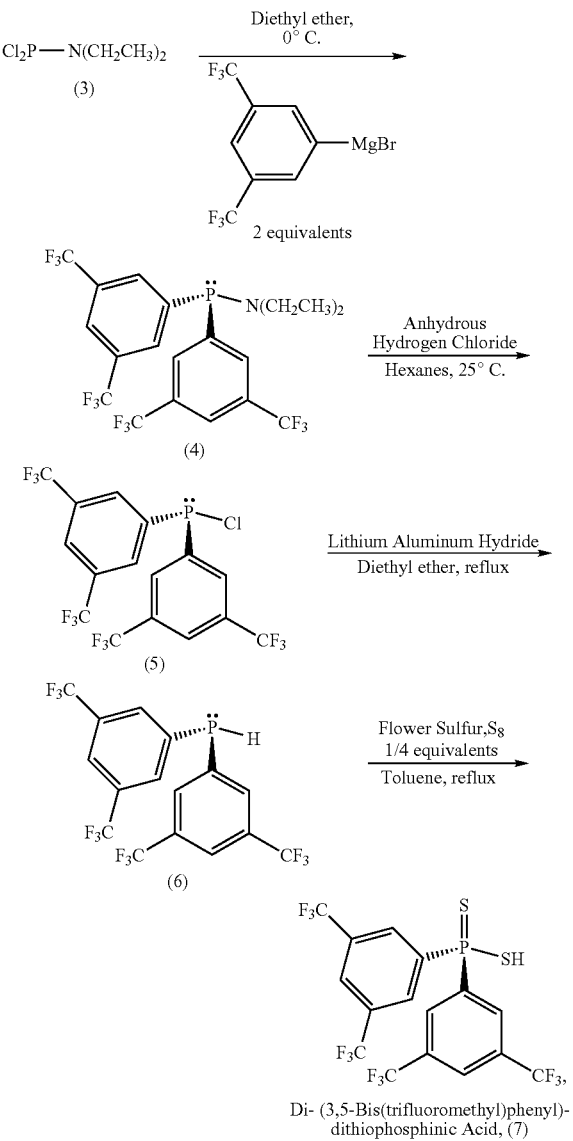

Scheme 2. Di- (3,5-Bis(trifluoromethyl)phenyl)dithiophosphinic Acid Synthesis

Di- (3,5-Bis(trifluoromethyl)phenyl)-dithiophosphinic Acid, (7)

Synthesis of Bis-(o-trifluoromethylphenyl)dithiophosphinic Acid

The following synthesis example is made by reference to Schemes 3 and 4 set forth below. Magnesium metal shavings (Mg°, 6.1 g; 0.25 mol) were placed into a 250-mL round-bottom flask. The flask was equipped with a gas inlet adapter and magnetic stir bar. This system was placed under vacuum and the system was then purged with nitrogen. First, 225 mL of anhydrous diethyl ether was transferred to the flask by syringe, and then 50 g (0.222 mol) of o-(CF$_3$)C$_6$H$_4$Br (8) was introduced by syringe. The solution was stirred during the reaction. An ice bath was needed to cool down the reaction as the magnesium was consumed. After most of the magnesium metal was consumed, the reaction mixture was allowed to set overnight under nitrogen. An ~1.0 M solution of o-(CF$_3$)C$_6$H$_4$MgBr (9) was produced.

Following a similar procedure as before and by reference to Scheme 4, a 500-mL three-neck, round-bottom flask, equipped with a gas inlet, a 125-mL addition funnel, magnetic stir bar, and a rubber septum was charged with nitrogen, PCl$_3$ (5 mL, 7.6 g, 0.055 mol), and anhydrous tetrahydrofuran (THF, 300 mL). The Grignard reagent, o-(CF$_3$)C$_6$H$_4$MgBr (9) (~1.0 M in diethyl ether, 110 mL, 0.110 mol), was added to the addition funnel via syringe and then slowly added to the solution at room temperature. After finishing, the addition funnel was removed and replaced with a stopper. The mixture remained at room temperature while stirring overnight. The next day, approximately 50% of the ether/THF solution was removed under reduced pressure, leaving behind a slurry. The slurry was carefully washed three times with 200 mL of hexanes to precipitate the salts. The supernatant, (o-(CF$_3$)C$_6$H$_4$)$_2$P—Cl (10), was decanted into a nitrogen-purged, 1000-mL round-bottom flask equipped with a magnetic stir bar. The hexanes were removed at reduced pressure, leaving an oil. The concentrated solution was then purified by vacuum distillation at 0.125 mmHg/110-120° C. to give (o-(CF$_3$)C$_6$H$_4$)$_2$P—Cl (10) as a colorless liquid. Isolated yields for compound (10) were roughly 62% with good purity as determined by P NMR.

The next reaction followed a similar procedure as before. Typically, a three-neck, 250-mL round-bottom flask was equipped with a water-jacketed condenser, gas inlet adaptor, two stoppers, and magnetic stir bar. The system was then purged with nitrogen. Anhydrous diethyl ether (100 mL) was transferred to the flask, via syringe. LiAlH$_4$ (0.76 g, 0.02 mol) was introduced into the flask and cooled to −78° C. A solution of (o-(CF$_3$)C$_6$H$_4$)$_2$P—Cl (10) (5.0 g, 0.014 mol) in anhydrous diethyl ether (25 mL) was slowly added to the cooled flask by syringe. The gray slurry was refluxed for 2 hours, cooled to 0° C., and slowly hydrolyzed with 10 wt % aqueous NH$_4$Cl. The organic layer was separated, and the remaining white precipitate was extracted three times with 25 mL of diethyl ether. The combined ether extracts were dried with Na$_2$SO$_4$; filtered; and evaporated to give (o-(CF$_3$)C$_6$H$_4$)$_2$P—H (11) as a pale yellow air-sensitive liquid. The concentrated solution was purified by vacuum distillation at 0.05 to 0.15 mmHg/88-93° C. to give (o-(CF$_3$)C$_6$H$_4$)$_2$P—H (11) as a colorless liquid. Isolated yields for compound (11) were roughly 61% with good purity as determined by $^{31}$P NMR. Compound (11) remains a liquid at room temperature.

The final reaction followed a similar procedure as before. A 100-mL round-bottom flask was equipped with a water-jacketed condenser, gas inlet adaptor, and magnetic stir bar. The system was purged with nitrogen. An excess of sulfur flower (S$_8$; 0.576 g, 0.018 mol) was used with this reaction. The sulfur added directly to the flask and then anhydrous toluene (50 mL) was transferred to the flask, via syringe. (o-(CF$_3$)C$_6$H$_4$)$_2$P—H (11) (2.0 g, 0.006 mol) was slowly added to the flask by syringe. The reaction was refluxed vigorously to yield (o-(CF$_3$)C$_6$H$_4$)$_2$PS$_2$H (12) in about 24 hours. The reaction was cooled to room temperature and the excess sulfur was filtered. Toluene was evaporated by reduced pressure to give a greenish-white solid. The solid residue was dissolved in diethyl ether, and more sulfur precipitated out of solution. The diethyl ether solution was filtered again to give a slight-green solution. The diethyl ether was removed by reduced pressure to give compound (11). Compound (11) has a $^{31}P$ NMR at 58 ppm, and it could be purified by vacuum distillation at 0.07-0.125 mmHg/150-160° C. It should be noted that the product needed to be "flashed" (heated glass) across to stop the product from solidifying in the distillation apparatus. It distilled as a white, amorphous solid. It can be crystallized in hexanes to give clear, transparent, hexagonal crystals. The final product yields for this reaction were variable between 30-53%.

The resulting Bis-(o-Bistrifluoromethylphenyl)dithiophosphinic Acid (7) had the following characteristics: 53% yield; mp=93-94° C.; bp=0.07-0.125 mmHg/150-160° C.; $^{31}P$ NMR δ (CDCl$_3$)=(t, $J_{PF}$=19.6 Hz) 58.1; $^1$H NMR δ (CDCl$_3$)=(dd, $J_{PH}$=18.0 Hz, $J_{FH}$=9.0 Hz, H) 8.43, (m, 3H) 7.65-7.85, (s, H) 3.31; $^{13}$C NMR δ (CDCl$_3$)=(doublet, $J_{PC}$=78.5 Hz, ipso) 134.3, (doublet, $J_{PC}$=12.8 Hz, ortho) 134.2, (doublet, $J_{PC}$=3.0 Hz, para) 132.1, (doublet, $J_{PC}$=14.3 Hz, meta) 131.7, (doublet of quartets, $J_{PC}$=6.0 Hz, $J_{CF}$=38.5 Hz, ortho) 129.7, (multiplet, meta) 128.0, (quartet, $J_{CF}$=274.7 Hz, CF$_3$) 123.4.

Scheme 3. Grignard Synthesis

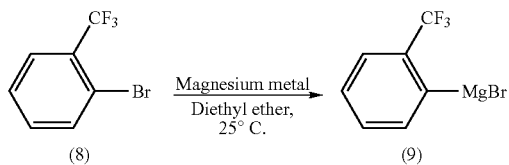

Scheme 4. Bis-(o-trifluoromethylphenyl)dithiophosphinic Acid Synthesis

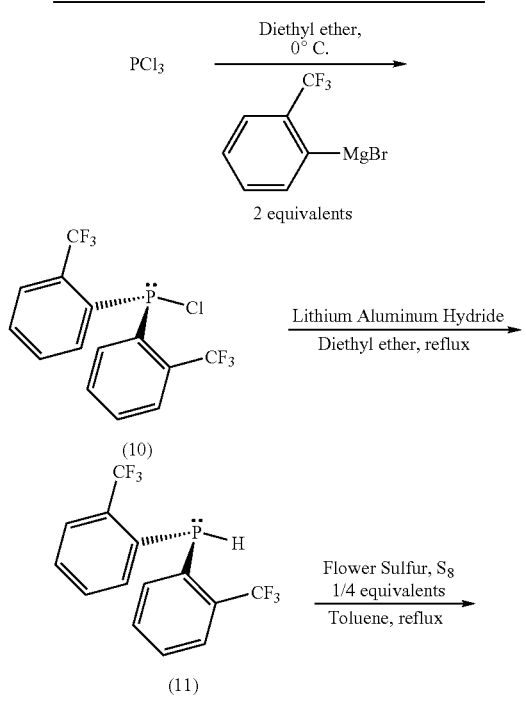

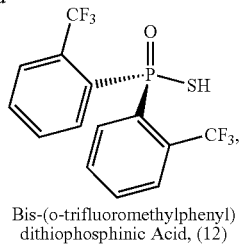

Bis-(o-trifluoromethylphenyl) dithiophosphinic Acid, (12)

The invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of forming an extraction agent for separation of actinides from lanthanides, comprising:

reacting a first reagent with a second reagent to produce (X)$_2$—R1-phosphine, the first reagent having a formula P—(X)$_3$ wherein X is a halogen, and the second reagent having a formula R1-(M1)X, wherein R1 is organic, M1 is a metal selected from the group consisting of magnesium, lithium, sodium, aluminum, zinc, cadmium, mercury, copper, lead, thallium, tin and combinations thereof, and X is a halogen;

reacting the (X)$_2$—R1-phosphine with a third reagent having a formula R2-(M1)X, wherein R2 is organic and X is a halogen, to produce R2—R1—X-phosphine;

reacting the R2—R1—X-phosphine with a metal hydride reagent having a formula (H)-M2, wherein M2 is a metal selected from the group consisting of lithium, sodium, potassium, magnesium, calcium, boron, aluminum, and combinations thereof, to produce R2—R1—H-phosphine; and reacting a source of sulfur with the R2—R1—H-phosphine to produce R2—R1-dithiophosphinic acid.

2. The method of claim 1, wherein each X is a halogen independently selected from the group consisting of fluorine, chlorine, bromine, and iodine.

3. The method of claim 1, wherein reacting a first reagent with a second reagent to produce (X)$_2$—R1-phosphine comprises reacting the first reagent and the second reagent in a solvent comprising diethyl ether at a temperature of about 0° C.

4. The method of claim 1, wherein reacting the (X)$_2$—R1-phosphine with a third reagent to produce R2—R1—X-phosphine comprises reacting the (X)$_2$—R1-phosphine and the R2-(M1)X in a solvent comprising diethyl ether at a temperature of about 0° C.

5. The method of claim 1, wherein reacting the R2—R1—X-phosphine with a metal hydride reagent comprises reacting a solvent comprising diethyl ether at reflux with lithium aluminum hydride and the R2—R1—X-phosphine to produce the R2—R1—H-phosphine.

6. The method of claim 1, wherein reacting a source of sulfur with the R2—R1—H-phosphine to produce R2—R1-dithiophosphinic acid comprises reacting the source of sulfur and the R2—R1—H-phosphine in toluene to produce the R2—R1-dithiophosphinic acid.

7. The method of claim 1, wherein R1 and R2 are independently selected from the group consisting of alkyl, alkenyl, alkynyl and aryl groups having from one carbon atom to twenty carbon atoms.

8. The method of claim 7, wherein the alkyl, alkenyl, alkynyl and aryl groups further comprise substituents selected from the group consisting of oxygen, nitrogen, fluorine, chlorine, bromine, iodine, boron, gallium, silicon, germanium, phosphorus, arsenic, antimony, sulfur, selenium, and tellurium, and oxides thereof.

9. The method of claim 7, wherein the aryl groups comprise single and multiple ring groups.

10. The method of claim 1, wherein the R2—R1-dithiophosphinic acid is asymmetrical.

11. A method for forming an extraction agent for separation of actinides from lanthanides, comprising:
    reacting a first reagent with a second reagent to produce R1—X—$R_{prot}$-phosphine, the first reagent having a formula P—$(X)_2$—$R_{prot}$ wherein X is a halogen and $R_{prot}$ is an organoamine comprising an alkyl group having from one carbon atom to five carbon atoms, the second reagent having a formula R1-(M1)X, wherein R1 is organic, M1 is a metal selected from the group consisting of magnesium, lithium, sodium, aluminum, zinc, cadmium, mercury, copper, lead, thallium, tin and combinations thereof, and X is a halogen;
    reacting the R1—X—$R_{prot}$-phosphine with a third reagent having a formula R2-(M1)X, wherein R2 is organic and X is a halogen, to produce R2—R1—$R_{prot}$-phosphine;
    reacting the R2—R1—$R_{prot}$-phosphine with a fourth reagent having a formula H—X wherein X is a halogen to produce R2—R1—X-phosphine;
    reacting the R2—R1—X-phosphine with a metal hydride reagent having a formula H-(M2) wherein M2 is a metal selected from the group consisting of lithium, sodium, potassium, magnesium, calcium, boron, aluminum and combinations thereof to produce R2—R1—H-phosphine; and
    reacting a source of sulfur with the R2—R1—H-phosphine in toluene to produce R2—R1-dithiophosphinic acid.

12. The method of claim 11, wherein each X is a halogen independently selected from the group consisting of fluorine, chlorine, bromine, and iodine.

13. The method of claim 11, wherein reacting a first reagent with a second reagent to produce R1—X—$R_{prot}$-phosphine comprises reacting the first reagent and the second reagent in a solvent comprising diethyl ether at a temperature of about 0° C.

14. The method of claim 11, wherein reacting the R1—X—$R_{prot}$-phosphine with a third reagent having a formula R2-(M1)X comprises reacting the R1—X—$R_{prot}$-phosphine and the R2-(M1)X in a solvent comprising diethyl ether at a temperature of about 0° C.

15. The method of claim 11, wherein reacting the R2—R1—$R_{prot}$-phosphine with a fourth reagent comprises reacting the R2—R1—$R_{prot}$-phosphine and the fourth reagent in hexane at a temperature of about 25° C. to produce the R2—R1-X-phosphine.

16. The method of claim 11, wherein reacting the R2—R1—X-phosphine with a metal hydride reagent comprises reacting the R2—R1—X-phosphine with lithium aluminum hydride in diethyl ether at reflux to produce the R2—R1—H-phosphine.

17. The method of claim 11, wherein each of R1 and R2 are independently selected from the group consisting of alkyl, alkenyl, alkynyl, and aryl groups having from one carbon atom to twenty carbon atoms.

18. The method of claim 17, wherein the alkyl, alkenyl, alkynyl, and aryl groups further comprise substituents selected from the group consisting of oxygen, nitrogen, fluorine, chlorine, bromine, iodine, boron, gallium, silicon, germanium, phosphorus, arsenic, antimony, sulfur, selenium, and tellurium, and oxides thereof.

19. The method of claim 17, wherein the aryl groups include single and multiple ring groups.

20. The method of claim 11, wherein the R2—R1-dithiophosphinic acid is asymmetrical.

21. The method of claim 11, wherein the R2—R1-dithophosphinic acid is symmetrical.

22. A method of forming an asymmetrical extraction agent for separation of actinides from lanthanides in an acidic medium, comprising:
    reacting o-trifluoromethylphenylmagnesium bromide with phosphorus trichloride to produce dichloro(o-trifluoromethylphenyl) phosphine;
    reacting the dichloro(o-trifluoromethylphenyl) phosphine with n-octylmagnesium bromide to produce chloro(n-octyl)(o-trifluoromethylphenyl) phosphine;
    reacting the chloro(n-octyl)(o-trifluoromethylphenyl) phosphine with lithium aluminum hydride to produce (n-octyl)(o-trifluoromethylphenyl) phosphine; and
    reacting a source of sulfur with the (n-octyl)(o-trifluoromethylphenyl) phosphine to produce (n-octyl)(o-trifluoromethylphenyl) dithiophosphinic acid.

23. A method of forming an asymmetrical extraction agent for separation of actinides from lanthanides in an acidic medium, comprising:
    reacting a source of o-trifluoromethylphenylmagnesium bromide with dichloro(diethylamino) phosphine to produce chloro(diethylamino)(o-trifluoromethylphenyl) phosphine;
    reacting the chloro(diethylamino)(o-trifluoromethylphenyl) phosphine with n-octylmagnesium bromide to produce (diethylamino)(n-octyl)(o-trifluoromethylphenyl) phosphine;
    reacting the (diethylamino)(n-octyl)(o-trifluoromethylphenyl) phosphine with anhydrous hydrogen chloride to produce chloro(n-octyl)(o-trifluoromethylphenyl) phosphine;
    reacting the chloro(n-octyl)(o-trifluoromethylphenyl) phosphine with lithium aluminum hydride to produce (n-octyl)(o-trifluoromethylphenyl) phosphine; and
    reacting a source of sulfur with the (n-octyl)(o-trifluoromethylphenyl) phosphine to produce (n-octyl)(o-trifluoromethylphenyl) dithiophosphinic acid.

24. A method of forming an extraction agent for separation of actinides from lanthanides, comprising:
    reacting a first reagent with a second reagent to produce $(R1)_2$—$R_{prot}$-phosphine, the first reagent having a formula P—$(X)_2$—$R_{prot}$ wherein X is a halogen and $R_{prot}$ is an organoamine comprising an alkyl group having from one carbon atom to five carbon atoms, and the second reagent having a formula R1-(M1)X wherein R1 is organic, M1 is a metal selected from magnesium, lithium, sodium, aluminum, zinc, cadmium, mercury, copper, lead, thallium, tin and combinations thereof, and X is a halogen;
    reacting the $(R1)_2$—$R_{prot}$-phosphine with a third reagent having a formula H—X to produce $(R1)_2$—X-phosphine, wherein X is a halogen;
    reacting a metal hydride reagent having a formula H-(M2) with the $(R1)_2$—X-phosphine to produce $(R1)_2$—H-phosphine, wherein M2 is a metal selected from the group consisting of lithium, sodium, potassium, magnesium, calcium, boron, aluminum, and combinations thereof; and reacting a source of sulfur with the $(R1)_2$—H-phosphine to produce $(R1)_2$-dithiophosphinic acid.

25. The method of claim 24, wherein the $(R1)_2$-dithiophosphinic acid is symmetrical and can operate in an acidic media of less than about a pH of 7.

26. The method of claim 24, wherein X is a halogen selected from the group consisting of fluorine, chlorine, bromine, and iodine.

27. The method of claim 24, wherein reacting a first reagent with a second reagent to produce $(R1)_2$—$R_{prot}$-phosphine comprises reacting the first reagent and the second reagent in a solvent comprising diethyl ether at a temperature of about 0° C.

28. The method of claim 24, wherein reacting a metal hydride reagent having a formula H-(M2) with the $(R1)_2$—X-phosphine to produce $(R1)_2$—H-phosphine comprises reacting the metal hydride reagent and the $(R1)_2$—X-phosphine in a solvent comprising diethyl ether at a temperature of about 0° C.

29. The method of claim 24, wherein reacting the $(R1)_2$—$R_{prot}$-phosphine with a third reagent having a formula H—X to produce $(R1)_2$—X-phosphine comprises reacting the $(R1)_2$—$R_{prot}$-phosphine with the third reagent in a solvent comprising hexane at a temperature of about 25° C.

30. The method of claim 24, wherein R1 is selected from the group consisting of alkyl, alkenyl, alkynyl, and aryl groups having from one carbon atom to twenty carbon atoms.

31. The method of claim 30, wherein the alkyl, alkenyl, alkynyl and aryl groups further comprise substituents selected from oxygen, nitrogen, fluorine, chlorine, bromine, iodine, boron, gallium, silicon, germanium, phosphorus, arsenic, antimony, sulfur, selenium, and tellurium, and oxides thereof.

32. The method of claim 31, wherein the aryl groups include single and multiple ring groups.

33. A method for forming an extraction agent for separation of actinides from lanthanides, comprising:

reacting a first reagent with a second reagent to produce $(R1)_2$—X-phosphine, the first reagent having a formula P—$(X)_3$, wherein X is a halogen, and the second reagent having a formula R1-(M1)X wherein R1 is an organic group comprising an inorganic component, M1 is a metal selected from the group consisting of magnesium, lithium, sodium, aluminum, zinc, cadmium, mercury, copper, lead, thallium, tin and combinations thereof, and X is a halogen;

reacting a metal hydride reagent having a formula H-M2 with the $(R1)_2$—X-phosphine, wherein M2 is a metal selected from the group consisting of lithium, sodium, potassium, magnesium, calcium, boron, aluminum, and combinations thereof, to produce $(R1)_2$—H-phosphine; and reacting a source of sulfur with the $(R1)_2$—H-phosphine to produce $(R1)_2$-dithiophosphinic acid.

34. The method of claim 33, wherein the $(R1)_2$-dithiophosphinic acid is symmetrical and can operate in an acidic medium at a pH of less than about 7.

35. The method of claim 33, wherein X is a halogen selected from the group consisting of fluorine, chlorine, bromine, and iodine.

36. The method of claim 33, wherein reacting a first reagent with a second reagent to produce $(R1)_2$—X-phosphine comprises reacting the first and second reagents in a solvent comprising diethyl ether at a temperature of about 0° C.

37. The method of claim 33, wherein reacting a metal hydride reagent having a formula H-M2 with the $(R1)_2$—X-phosphine comprises reacting the metal hydride reagent and the $(R1)_2$—X-phosphine in a solvent comprising diethyl ether at a temperature of about 0° C.

38. The method of claim 33, wherein R1 is an alkyl, alkenyl, alkynyl, or aryl group having from one carbon atom to twenty carbon atoms.

39. The method of claim 38, wherein the alkyl, alkenyl, alkynyl, or aryl group further comprises inorganic components selected from the group consisting of oxygen, nitrogen, fluorine, chlorine, bromine, iodine, boron, gallium, silicon, germanium, phosphorus, arsenic, antimony, sulfur, selenium, and tellurium, and oxides thereof.

40. The method of claim 38, wherein the aryl group includes single or multiple ring groups.

41. A method of forming a symmetrical extraction agent for separation of actinides from lanthanides in acidic medium, comprising:

reacting o-trifluoromethylphenylmagnesium bromide with phosphorus trichloride to produce chloro(di-o-trifluoromethylphenyl) phosphine;

reacting the chloro(di-o-trifluoromethylphenyl) phosphine with lithium aluminum hydride to produce (di-o-trifluoromethylphenyl) phosphine; and reacting a source of sulfur with the (di-o-trifluoromethylphenyl) phosphine to produce (di-o-trifluoromethylphenyl) dithiophosphinic acid.

42. A method of forming a symmetrical extraction agent for separation of actinides from lanthanides, comprising:

reacting o-trifluoromethylphenylmagnesium bromide with dichloro(diethylamino) phosphine to produce (diethylamino)(di-o-trifluoromethylphenyl) phosphine;

reacting the (diethylamino)(di-o-trifluoromethylphenyl) phosphine with anhydrous hydrogen chloride to produce chloro(di-o-trifluoromethylphenyl) phosphine;

reacting the chloro(di-o-trifluoromethylphenyl) phosphine with lithium aluminum hydride to produce (di-o-trifluoromethylphenyl) phosphine; and reacting a source of sulfur with the (di-o-trifluoromethylphenyl) phosphine to produce (di-o-trifluoromethylphenyl) dithiophosphinic acid.

* * * * *

UNITED STATES PATENT AND TRADEMARK OFFICE
CERTIFICATE OF CORRECTION

PATENT NO. : 7,704,468 B1  
APPLICATION NO. : 11/232541  
DATED : April 27, 2010  
INVENTOR(S) : John R. Klaehn et al.

Page 1 of 1

It is certified that error appears in the above-identified patent and that said Letters Patent is hereby corrected as shown below:

In the specification:
  COLUMN 9,   LINE 25,    change "n-octyl" to --(n-octyl)--

Signed and Sealed this  
First Day of October, 2013

Teresa Stanek Rea  
*Deputy Director of the United States Patent and Trademark Office*